United States Patent [19]
Buchbinder et al.

[11] Patent Number: 5,125,895
[45] Date of Patent: * Jun. 30, 1992

[54] STEERABLE CATHETER
[75] Inventors: Maurice Buchbinder; Ronald J. Solar, both of San Diego, Calif.
[73] Assignee: Medtronic Versaflex, Inc., Minneapolis, Minn.
[*] Notice: The portion of the term of this patent subsequent to Feb. 9, 2005 has been disclaimed.
[21] Appl. No.: 287,522
[22] Filed: Dec. 19, 1988

Related U.S. Application Data

[63] Continuation of Ser. No. 130,747, Dec. 9, 1987, abandoned, which is a continuation of Ser. No. 888,813, Jul. 22, 1986, Pat. No. 4,723,936.
[51] Int. Cl.$^5$ .................. A61M 37/00; A61M 29/00
[52] U.S. Cl. .................................. 604/95; 604/96
[58] Field of Search .................... 604/95-99, 604/104-109; 606/191-192

[56] References Cited

U.S. PATENT DOCUMENTS

| | | |
|---|---|---|
| D. 274,470 | 6/1984 | Lundquist . |
| 1,060,665 | 5/1913 | Bell . |
| 2,498,692 | 2/1950 | Mains . |
| 2,574,840 | 11/1951 | Pieri et al. . |
| 2,688,329 | 9/1954 | Wallace . |
| 2,707,958 | 5/1955 | Davis . |
| 3,058,473 | 10/1962 | Whitehead . |
| 3,470,876 | 10/1969 | Barchilon . |
| 3,521,620 | 7/1970 | Cook . |
| 3,547,103 | 12/1970 | Cook . |
| 3,605,725 | 9/1971 | Bentov . |
| 3,625,200 | 12/1971 | Muller . |
| 3,776,222 | 12/1973 | Smiddy . |
| 3,941,119 | 3/1976 | Corrales . |
| 4,020,829 | 3/1977 | Willson et al. . |
| 4,033,331 | 7/1977 | Guss et al. . |
| 4,044,765 | 8/1977 | Kline . |
| 4,150,676 | 4/1979 | Jackson . |
| 4,195,637 | 4/1980 | Grüntzig et al. . |
| 4,230,123 | 10/1980 | Hawkins, Jr. . |
| 4,231,715 | 11/1980 | Gleichner . |
| 4,245,624 | 1/1981 | Komiya . |
| 4,299,227 | 11/1981 | Lincoff . |
| 4,323,071 | 4/1982 | Simpson et al. . |
| 4,332,254 | 6/1982 | Lundquist . |
| 4,402,307 | 9/1983 | Hanson et al. . |
| 4,422,447 | 12/1983 | Schiff . |
| 4,439,185 | 3/1984 | Lundquist . |
| 4,444,188 | 4/1984 | Bazelle et al. . |
| 4,456,017 | 6/1984 | Miles . |
| 4,487,206 | 12/1984 | Aagard . |
| 4,509,945 | 4/1985 | Kramann et al. . |
| 4,516,972 | 5/1985 | Samson . |
| 4,545,390 | 10/1985 | Leary ............... 604/95 |
| 4,554,929 | 11/1985 | Samson et al. ........... 604/95 |
| 4,571,239 | 2/1986 | Heyman . |
| 4,571,240 | 2/1986 | Samson et al. . |
| 4,573,470 | 3/1986 | Samson et al. . |
| 4,582,181 | 4/1986 | Samson . |
| 4,586,923 | 5/1986 | Gould et al. . |
| 4,601,705 | 7/1986 | McCoy . |
| 4,616,652 | 10/1986 | Simpson . |
| 4,619,263 | 10/1986 | Frisbie et al. . |
| 4,619,274 | 10/1986 | Morrison . |
| 4,624,657 | 11/1986 | Gould et al. . |
| 4,641,654 | 2/1987 | Samson et al. . |
| 4,650,467 | 3/1987 | Bonello et al. . |
| 4,664,657 | 5/1987 | Williamitis et al. . |
| 4,723,936 | 2/1988 | Buchbinder et al. ............. 604/95 |
| 4,724,846 | 2/1988 | Evans, III ............... 604/95 |
| 4,732,163 | 3/1988 | Bonello et al. ........... 604/95 |
| 4,734,093 | 3/1988 | Bonello et al. ........... 604/95 |

FOREIGN PATENT DOCUMENTS

| | | |
|---|---|---|
| 361108 | 11/1978 | Austria . |
| 8301893 | 6/1983 | European Pat. Off. . |
| 182689 | 5/1986 | European Pat. Off. . |
| 223176 | 5/1987 | European Pat. Off. . |
| 1116317 | 8/1966 | United Kingdom . |

Primary Examiner—C. Fred Rosenbaum
Assistant Examiner—Mark Bockelman
Attorney, Agent, or Firm—Harold R. Patton; Sandra S. Schultz; John L. Rooney

[57] ABSTRACT

This invention relates to steerable catheters. More particularly, this invention relates to steerable catheters comprising a flexible catheter comprising a spring coil body defining a lumen, the spring coil body having a flexible covering thereon; a deflection wire, the distal end of the deflection wire being attached to the distal end of the spring coil body; and control means attached to the proximal end of the catheter, the proximal end of the deflection wire extending through the control means and the control means having a torque means which fixedly engages said deflection wire.

40 Claims, 7 Drawing Sheets

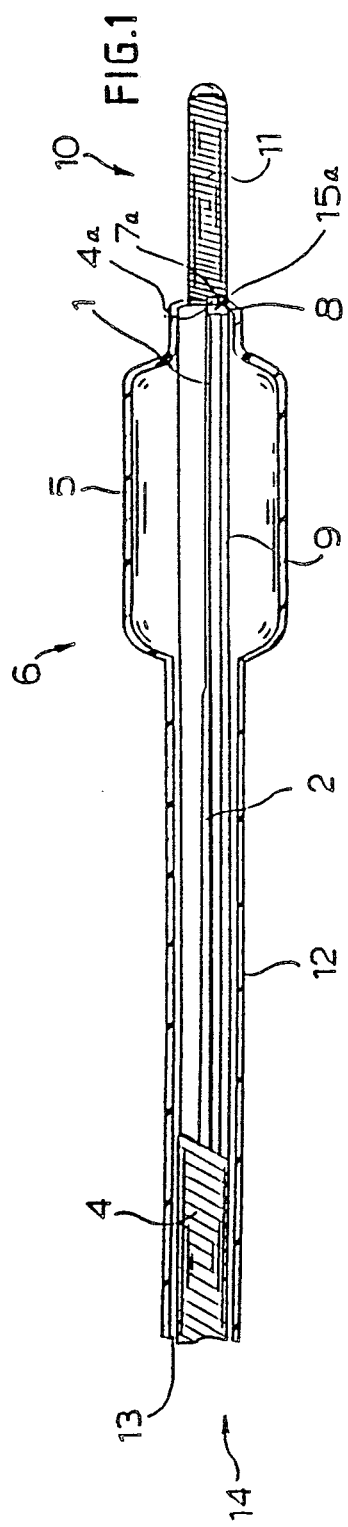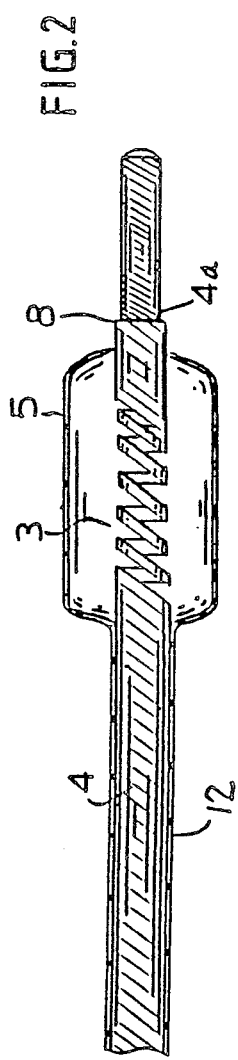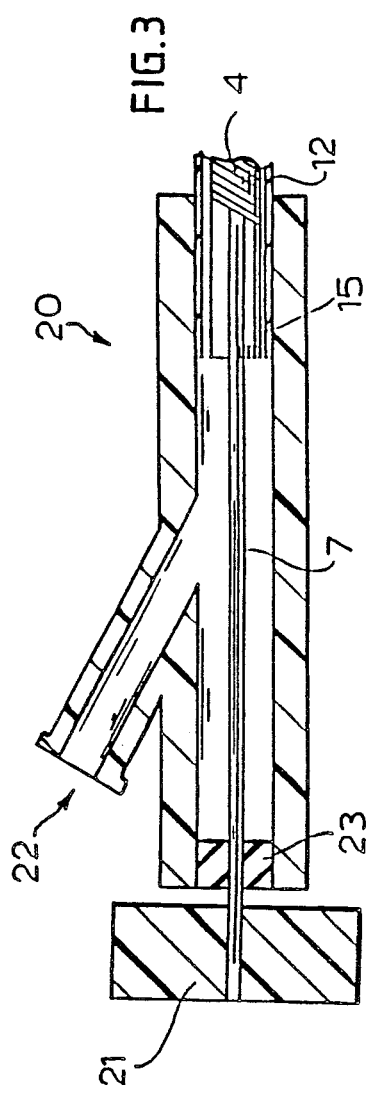

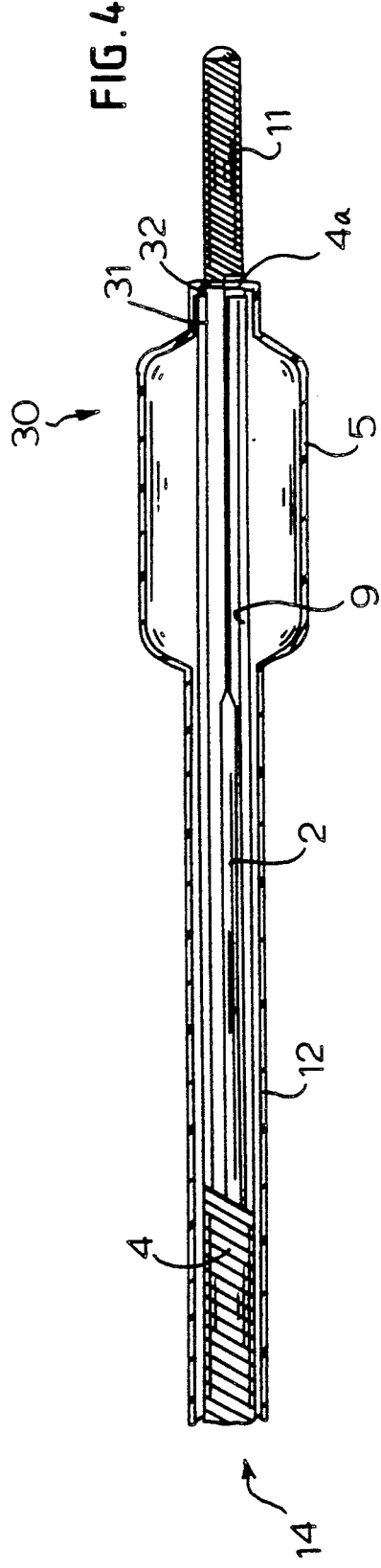
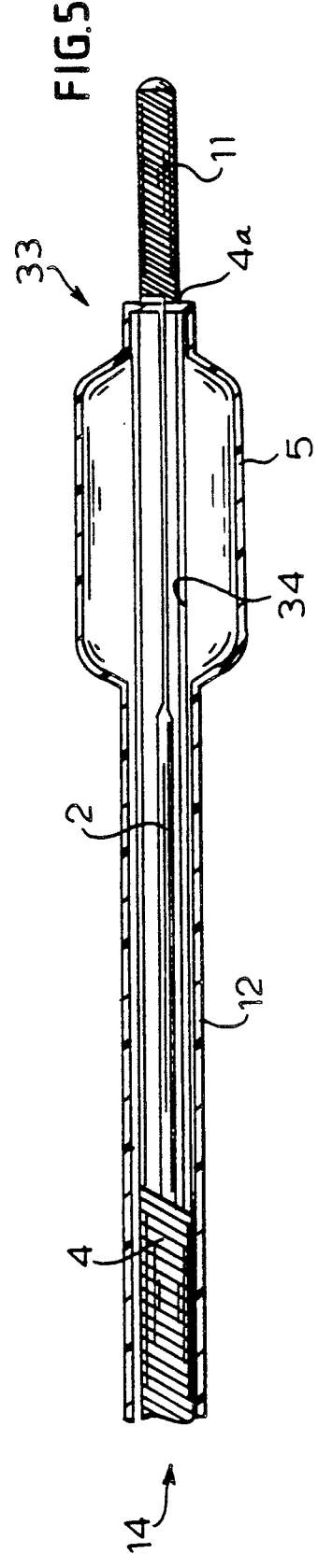
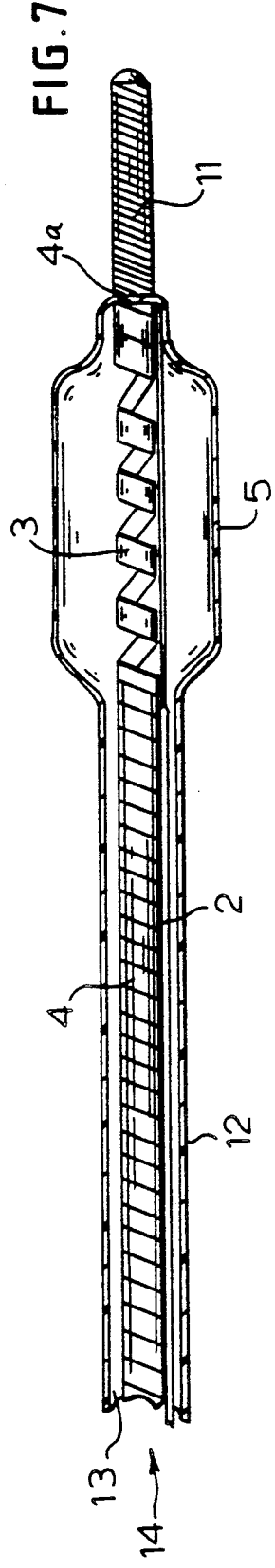

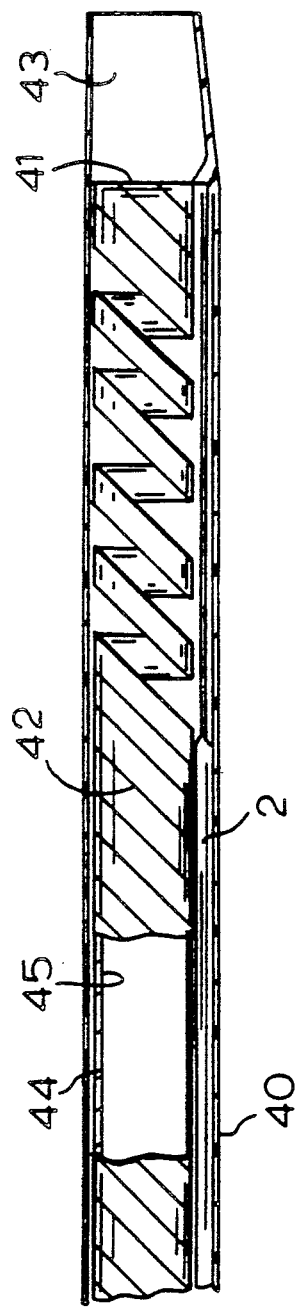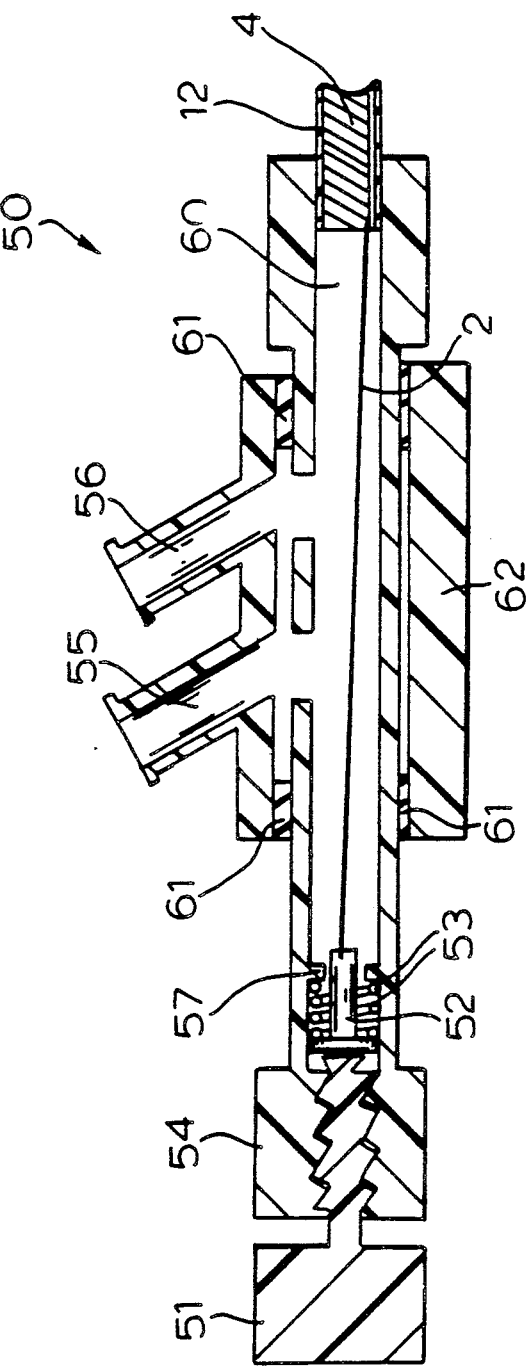

STEERABLE CATHETER

This patent application is a continuation of U.S. patent application Ser. No. 130,747, filed Dec. 09, 1987 now abandoned, which is a continuation of U.S. patent application Ser. No. 888,813 filed Jul. 22, 1986 now U.S. Pat. No. 4,723,936.

FIELD OF THE INVENTION

This invention relates to steerable catheters. More particularly, this invention relates to steerable catheters having improved directionality.

BACKGROUND OF THE INVENTION

Catheters comprise tube-like members that are inserted into the body for various medical reasons, some diagnostic and others therapeutic. While in many instances the steerability or directionality of such catheters is of concern, steerability is particularly important with regard to certain urological or cardiovascular applications.

There have been various attempts to develop steerable catheters. For example, U.S. Pat. No. 1,060,665 describes an early attempt to provide a catheter capable of some direction. However, the device disclosed in this patent, as well as catheters and catheter guides disclosed in later patents, such as U.S. Pat. Nos. 2,574,840 and 2,688,329, tend to be characterized by only limited directionality.

In addition, some supposedly steerable catheters are too large and rigid to be of practical use in cardiovascular techniques. See, for example, U.S. Pat. Nos. 3,470,876 and 3,605,725, where wires equidistantly positioned along the length of a catheter are connected to a steering means which pulls on the wires to cause the distal end of the catheter to go in a desired direction. Moreover, U.S. Pat. Nos. 3,521,620, 3,547,103, 3,625,200, and 4,020,829 describe coil spring guide wires that have a certain degree of directionality but are too rigid for safe usage in certain delicate cardiovascular procedures.

According to U.S. Pat. No. 4,033,331, a coronary catheter has a main lumen and a shaping wire lumen. When the wire is withdrawn through the shaping wire lumen, the catheter assumes certain predetermined configurations. While this so-called steerable catheter is useful in some cardiovascular applications, such as positioning the initial guiding catheter guide through which other devices are guided, its limited directionality and limited tip control preclude extensive use.

A medical procedure known as percutaneous transluminal coronary angioplasty (PTCA) was developed in approximately 1976-1977 by Dr. Andreas Gruntzig. According to this procedure, blockage in a coronary artery can be reduced by positioning a balloon dilatation catheter across the blockage and the inflating the balloon, which causes the blockage to decrease. Such positioning requires that the balloon dilatation catheter be "steered" into place, that is, across the stenotic lesion causing the blockage, by manipulation at the proximal end of the catheter.

The procedure is actually somewhat complex, consisting of introducing a catheter system via the femoral or brachial artery under local anesthesia. A pre-shaped guiding catheter is positioned into the orifice of the coronary artery, and through this guiding catheter a second dilatation catheter is advanced into the branches of the coronary artery. The dilatation catheter has an elliptically shaped balloon portion near the tip which can be inflated and deflated. After traversal of the stenotic lesion of the coronary artery, the balloon portion is inflated with fluid, which dilates the lumen of the vessel.

The PTCA procedure and equipment have become increasingly refined over the past six years. The first marketable PTCA apparatus consisted of a small catheter with a single balloon port and no central lumen, that is, a so-called "fixed wire" system, which terminated in lateral openings at the distal end thereof. This system, which is the subject of U.S. Pat. No. 4,195,637, was designed by Dr. Gruntzig and was marketed in the United States by USCI. The fixed wire catheter system disclosed in U.S. Pat. No. 4,195,637 comprises a balloon dilatation catheter and a low friction guide catheter consisting of one tubular member fitted into a more rigid, shrunk-on tubular member that is not co-extensive. The distal end of the balloon dilatation catheter has a flexible tip advantageously fabricated from a spring steel wire.

In 1980-1981 Dr. John Simpson, working at Stanford University, began to modify the fixed wire system and eventually developed a catheter with a free central lumen for movable guide wires. This catheter system is the subject of U.S. Pat. No. 4,323,071, which is assigned to Advanced Cardiovascular Systems, Inc. (ACS), formerly known as Advanced Catheter Systems, Inc. By use of such a movable wire system, one could more readily select the desired coronary artery and reach smaller branches since the movable guide wires are inherently smaller and more flexible than the fixed wire system. Subsequent to the development of the catheter with movable guide wires, known as the Simpson-Robert system and marketed by ACS, USCI has abandoned the fixed wire system and has marketed a similar device, calling it the steerable catheter, DILACA ®.

Samson, U.S. Pat. No. 4,516,972 issued May 14, 1985, to ACS. This patent is directed to a guide catheter having a helically wound ribbon of flexible material imbedded in the wall of the catheter to provide torsional rigidity.

There is a further catheter system in use known as the Hartzler low profile catheter system. According to this catheter system a balloon dilatation catheter has a concentrically contained guide wire extending the length of said catheter. Moreover, the distal end of the guide wire extends a short distance beyond the distal end of the balloon dilatation catheter and is affixed to the distal end of the balloon dilatation catheter.

The catheter system with movable guide wires and the low profile catheter system each represent an advance but still have disadvantages such as limited steerability, which is at present dependent upon the torquability, or torque control, of the movable wire. Steerability is highly significant in a cardiovascular procedure such as PTCA, or angioplasty, because less steerability results in greater time spent in the body and more possible patient trauma. Multiple insertions of guide wires and catheters can lead to thrombosis in that coagulation may commence along a guide wire surface and be forced into the heart when a catheter is slid over the guide wire. Furthermore, there are some blockages which simply can't be reached with presently known equipment.

There has been a need for more steerable catheter means, especially means useful in a procedure such as PTCA. Preferably such catheter means should have the following characteristics:
1. The distal end should have a pre-formed tip softer than the catheter shaft.
2. The entire catheter should be small enough to compare favorably with the already existing small dilatation catheters.
3. The catheter should be capable of rotational and deflective movement. Rotational movement of the steering tip should be precise enough to provide as close to 1:1 torque as possible. This would make the device very useful since it could ultimately be substituted for high torque wires already available.
4. The steering catheter means should optionally have a balloon inflation port.

U.S. patent application Ser. No. 651,806, filed Sep. 18, 1984, and U.S. patent application Ser. No. 774,345, filed Sep. 10, 1985, both of which are incorporated herein by reference, are directed to improved steerable catheter means useful in, for example, cardiovascular applications. The catheter means disclosed therein are characterized by a relatively low profile and enhanced directionality due to combined rotation of the catheter means and active deflection of the catheter tip.

OBJECTS OF THE INVENTION

It is an object of the invention to provide a steerable catheter.

It is also an object of the invention to provide a steerable catheter useful in cardiovascular applications.

It is a further object of the invention to provide a delivery means and a method of using said delivery means to deliver objects such as guide wires or balloons to various parts of the cardiac and vascular systems as well as of the body.

It is a yet further object of the invention to provide a steerable catheter means comprising:
a flexible catheter comprising a spring coil body defining a lumen, each of said catheter and said spring coil body, having proximal and distal ends and said spring coil body having a flexible covering thereon,
a deflection wire having proximal and distal ends and being substantially co-extensive with said spring coil body, the distal end of said deflection wire being attached to the distal end of said spring coil body, and
control means attached to the proximal end of said catheter, the proximal end of said deflection wire extending through the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means having rotation means capable of causing said catheter to rotate about its longitudinal axis.

These and other objects of the invention will become more apparent in the discussion below.

BRIEF DESCRIPTION OF THE DRAWINGS

FIG. 1 represents a partly cross-sectional planar view of the distal portion of an embodiment of the invention;

FIG. 2 represents a cross-sectional planar view of the embodiment shown in FIG. 1;

FIG. 3 represents a partly cross-sectional planar view of the proximal end of the embodiment shown in FIG. 1;

FIG. 4 represents a partly cross-sectional planar view of the distal portion of another embodiment of the invention;

FIG. 5 represents a partly cross-sectional planar view of the distal end of a variation of the embodiment shown in FIG. 4;

FIGS. 7 to 11 represent cross-sectional planar views of the distal portion of further embodiments of the invention; and FIGS. 12 to 14 each represent a partly cross-sectional view of the proximal end of an embodiment of the invention.

DETAILED DESCRIPTION OF THE INVENTION

Figure 6:
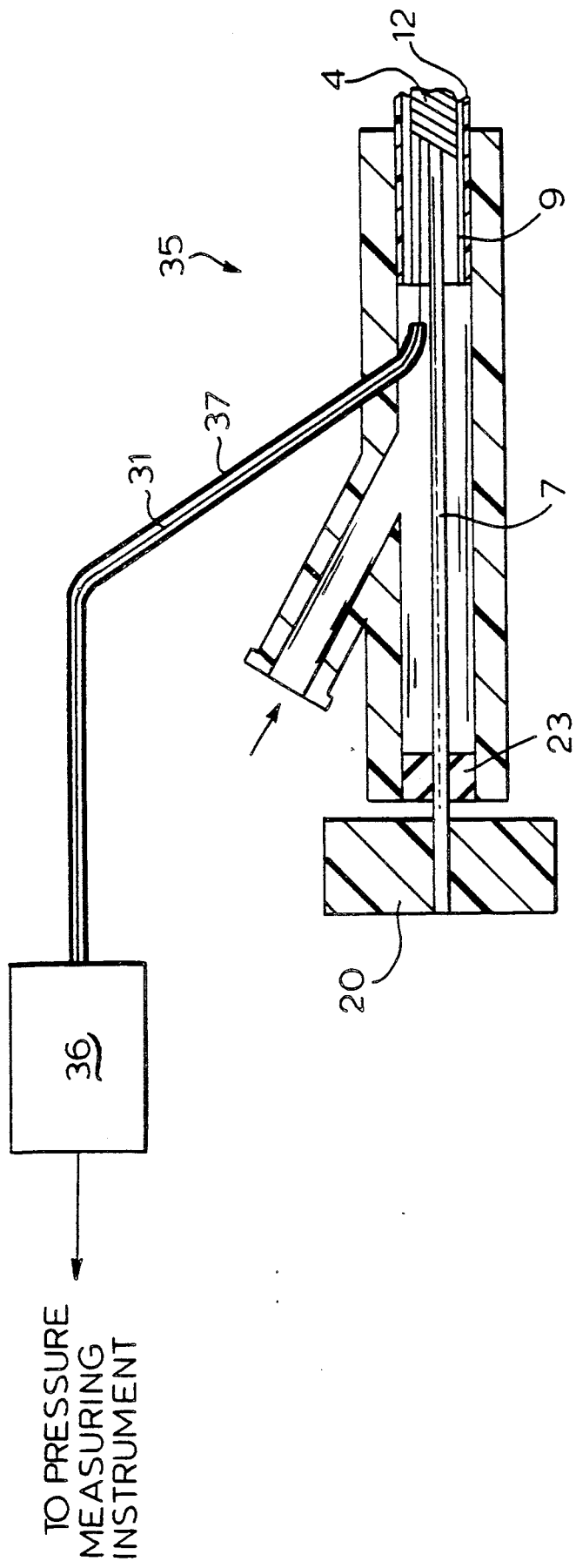
FIG. 6 represents a partly cross-sectional planar view of the proximal end of the embodiment shown in FIG. 4.

The invention disclosed herein is a catheter for human use having the type of steerability taught by the above-mentioned patent applications, but the method by which the movements are accomplished is unique. Steering is provided by a steering or deflection wire in conjunction with a spring coil body. Rotation of control means or a member of the control means at the proximal end of the catheter means results in torque being applied to the steering wire/spring coil body assembly, and the torque is transmitted to the distal end of the catheter means to cause rotation of the catheter tip to a desired position. The combination of a deflection wire and a spring coil body results in greater torque transmission than is achieved by each member alone, and the increased torque transmission results in a finer degree of tip control. Tip control is further refined by active deflection of the tip of the catheter out of plane during rotation.

At the point where bending of the tip is desired, the deflection wire is tapered to a smaller diameter and optionally the tension of the winding of the spring coil body is reduced ("looser wound"). Longitudinal movement, i.e., movement along the longitudinal axis of the catheter means, of the deflection wire, which is fixed at the distal tip, results in preferential bending at this point.

There are two major embodiments of the invention herein. One embodiment has a balloon for dilatation of strictures, and the other embodiment has a through lumen which allows passage of other devices, e.g., guidewires or catheters, and infusion of fluids, e.g., pharmaceuticals, radiopaque contrast agents, or the like, to perform various diagnostic and therapeutic procedures.

More specifically, the invention herein is directed to an eminently more flexible and steerable catheter or delivery means. Said means comprises a flexible catheter having distal and proximal ends and substantially one lumen, the lumen optionally being closed at its distal end. A deflection wire having distal and proximal ends extends the length of the catheter means through the lumen, and the distal end of the deflection wire is either embedded in the closed end of the lumen or attached to the distal end of the lumen. The lumen itself comprises a closely wound spring coil body, and the outer surface of the spring coil body is covered by substantially co-extensive tubing. Attached to the proximal end of the catheter is a control means, through which the proximal end of the deflection wire extends. An engaging means in the control means fixedly engages the proximal end of the steering wire.

The invention can perhaps be better understood by making reference to the drawings. In the embodiment of the invention shown in FIGS. 1 to 3, a tapered section 1 of the deflection wire 2 and a reduced tension section 3 of a spring coil body 4 are located at a balloon section 5 of a catheter, designated generally as 6. This configuration will result in preferential bending of the catheter 6 at the balloon section 5 when the tip deflecting control means is activated, i.e., when longitudinal forces are applied to the proximal end 7 of deflection wire 2. The distal end of the spring coil body 4 is closed at closure 4a, which closure may be a weld, a cap, solder, a braze, or, preferably, an adhesive such as a U.V. curing adhesive or cyano-acrylate bond. The distal end 7a of the steering wire 2 is bonded to closure 4a or to the interior surface of the distal end 8 of the spring coil body 4 by suitable means, e.g., mechanical means, adhesive, solder, braze, or weld. An anchor wire or safety wire 9 may optionally be included, as shown in FIG. 1. Anchor wire 9 may provide more pronounced bending or facilitate the return of the distal end or tip 10 of the catheter 6 to a straight position. The anchor wire 9, which is bonded to the spring coil body 4 at its proximal and distal ends 15 and 15a, respectively, may be made from any metal wire, preferably a high tensile strength circular wire of stainless steel having a diameter of from about 0.001 to 0.020 in. Optionally this wire may have a rectangular cross-section of from about 0.001 to 0.020 in. ✕ from about 0.001 to 0.040 in. Regardless of the shape of the cross-section, the distal end of the anchor wire 9 may be tapered, for example, to a diameter of from about 0.001 to 0.010.

Anchor wire 9 may optionally terminate at a point proximal from the distal end 15a of spring coil body 4. For example, the anchor wire 9 may terminate within spring coil body 4 at a point immediately proximal to the proximal portion of balloon section 5. The distal portion of the anchor wire 9 would then be bonded by suitable means, e.g., mechanical means, adhesive, solder, braze, or weld, to the interior surface of spring coil body 4.

To minimize vessel trauma and to facilitate catheter passage, the distal end 10 of the catheter 6 may have a spring guide tip 11, which is affixed or otherwise embedded in closure 4a. The guide tip 11 may be made from any suitable metal or plastic coil spring having a diameter of from about 0.005 to 0.500 in. A material opaque to x-rays, e.g., platinum, gold, tungsten, tantalum, or the like, is preferred since the guide tip 11 would then act as a fluoroscopic marker to aid in precise positioning of the balloon section 5 of the catheter 6.

To allow the catheter to infuse fluids or hold pressure, for example, in the case of inflating a dilatation balloon, the spring coil body 4 is covered with an impervious body skin or tubing 12. The body skin 12 may comprise one or more layers of suitable low friction polymeric material such as a polyolefin, a polytetrafluoroethylene such as TEFLON ®, polyvinyl chloride, or the like, and may be applied by any one of a variety of methods known to those skilled in the art. For example, heat shrinkable tubing may be heat shrunk onto the spring coil body 4; polymeric material may be sprayed on or coextruded; or a tube of body skin may simply be slid over the spring coil body 4. Heat shrinking heat shrinkable tubing is preferred.

For the dilatation catheters described herein, the body skin 12 may be integral with the balloon section 5, and the balloon section 5 may be suitably bonded to the body skin 12. In use, the balloon section 5 could be inflated via a space 13 between the spring coil body 4 and body skin 12 or, preferably, via the lumen 14 formed by the spring coil body 4.

According to an embodiment of the invention not shown, the catheter may have an first coating or skin extending substantially from the proximal end 15 of the spring coil body 4 to the distal end 15a thereof, and a second, outer coating forming balloon section 5. The outer coating would not necessarily be co-extensive with the first coating and might extend distally and proximally from balloon section 5 only to the extent necessary to form an appropriate seal with the first coating. The first coating would then require an opening in the area of balloon section 5 for inflation or deflation thereof.

A control means, designated generally as 20, to steer the catheter is shown in FIG. 3. Pushing or pulling deflection knob 21 causes the distal end 10 of the catheter 6 to deflect out of plane, that is, toward or away from the longitudinal axis of catheter 6. Rotation of the deflection knob 21 by itself or together with the entire control means 20 results in rotation of the catheter tip 10 to a desired orientation. An opening or port 22 in the control means 20 and a seal 23 allow fluid to be directed toward the distal end 10 of the catheter 6 for inflation of the balloon section 5.

Another embodiment of the invention, as represented in FIGS. 4 to 6, 8, and 10, comprises an optical fiber. The fiber is primarily intended for monitoring pressure such as arterial pressure; however, such a fiber may be employed for other applications, e.g., delivery of light or light energy (laser), visualization, etc. FIG. 4 shows a dilatation catheter, designated generally as 30, employing an optical fiber 31 having a pressure sensing membrane 32 at its distal end. The catheter, designated generally as 33, in FIG. 5 is similar, but there optical fiber 34 also serves the function of an anchor wire. As shown in FIG. 6, the optical fiber 31 exits a control means, generally designated as 35, to an electrical transducer or connector 36 that may transmit information from the optical fiber 31 to appropriate instrumentation (not shown). The portion of optical fiber 31 extending from control means 35 to electrical transducer 36 may be covered by protective jacketing 37, which may be comprised of any suitable, preferably flexible, elastomeric or polymeric material.

Figure 8:
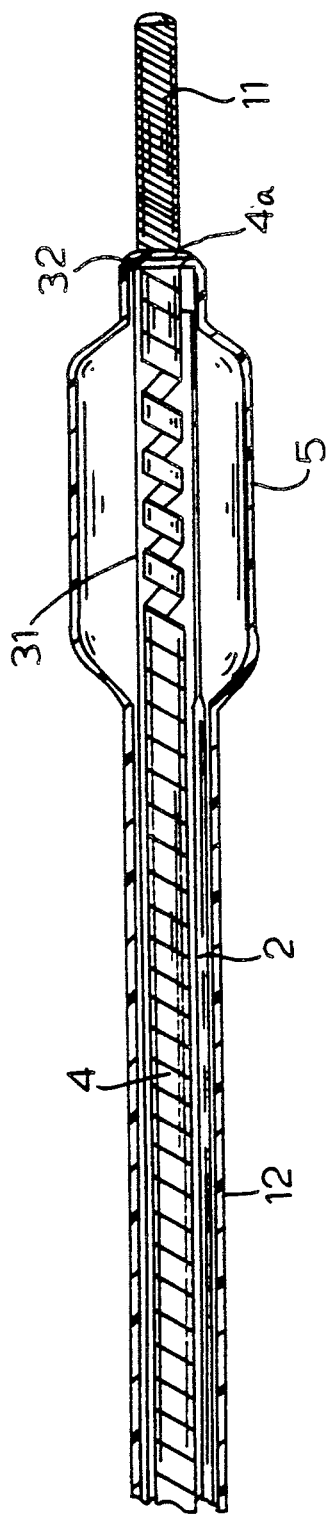

FIGS. 1 and 2 represent embodiments of the invention having the deflection wire 2 located within the lumen 14 of the spring coil body 4. Alternatively, deflection wire 2 could be located between the spring coil body 4 and the body skin 12, as shown in FIG. 7. An anchor wire (not shown) may or may not be used, and, as shown in FIG. 8, an optical fiber 31 having pressure sensing membrane 32 could also be employed in this construction. If an anchor wire is employed, it could be located either within lumen 14 or between the spring coil body 4 and the body skin 12.

As mentioned above, the spring coil body terminates in a closure means. When no guide tip is present, the closure means may comprise a mass of adhesive having a substantially semispherical or rounded shape in the distal direction. Also, the closure means could have a polymeric covering which functions as an atraumatic tip. In any event, the distal end of the catheter of this type should be soft or low friction, or both.

Figure 9:
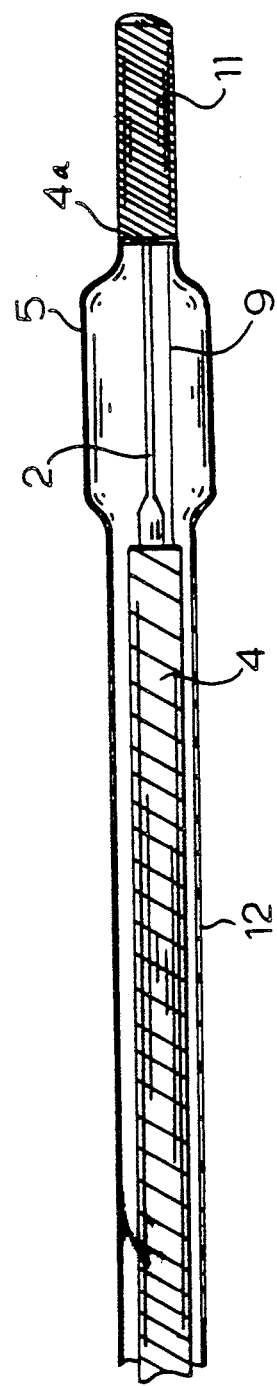
Figure 10:
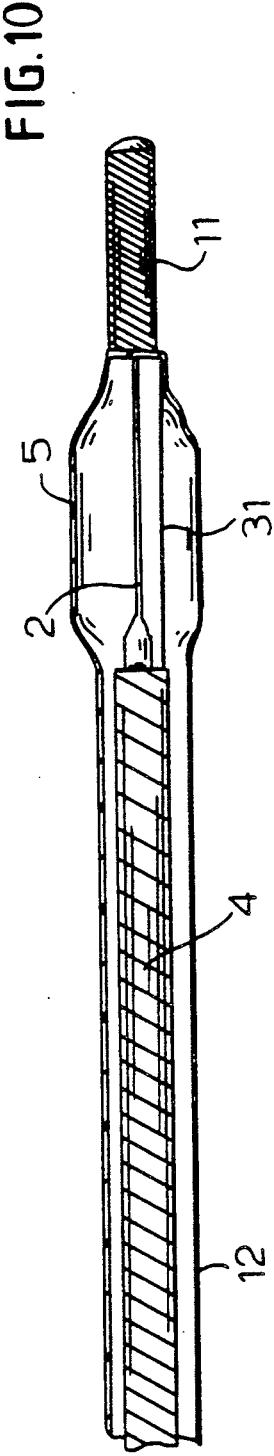

A further embodiment of the invention is shown in FIGS. 9 and 10. In these configurations the spring coil body 4 terminates proximally to the balloon section 5 such that only the tapered section 1 of the steering wire, and optionally the fine anchor wire and/or the optical fiber 31, is within the balloon section 5. Since the mass of material within the balloon is reduced as compared to, for example, the embodiment shown in FIG. 1, the deflated diameter or profile of the balloon section may be smaller. This will allow for passage through smaller strictures. The anchor wire 9, which is shown extending to spring tip 11, may be deleted altogether or it may be positioned between the spring coil body 4 and the body skin 12.

A yet further embodiment of the invention is shown in FIG. 11. The steering mechanism is similar to that of the device represented in FIG. 7, although the device depicted in FIG. 11 has additional intended uses. Whereas FIG. 7 shows a device intended for stricture dilatation, that shown in FIG. 11 is may be used for the delivery of other devices, e.g., catheters, guidewires, fiber optics, etc., and infusion of fluids, e.g., pharmaceuticals, radiopaque contrast agents, etc., to perform various diagnostic and therapeutic procedures.

The steering means for the embodiment shown in FIG. 11 has been described above. The body skin 40 extends beyond the distal end 41 of the spring coil body 42 to provide a soft, atraumatic, annular, i.e., cylindrical, tip 43, preferably made from a polytetrafluoroethylene such as TEFLON or another low friction polymeric material. An optional liner 44 provides a smooth surface for passage of other devices, such as mentioned above. The liner 44 is preferably made from TEFLON or another low friction polymeric material. The inner surface 45 of the liner 44 may be treated or grafted to improve lubrication, i.e., to reduce friction. This embodiment may optionally include an anchor wire 9 (not shown) and/or an optical fiber (not shown) between the spring coil body 42 and the body skin 40. In addition, this embodiment may exclude deflection wire 2 and/or include balloon dilatation means positioned concentrically around the distal portion of spring coil body 42.

Figure 13:
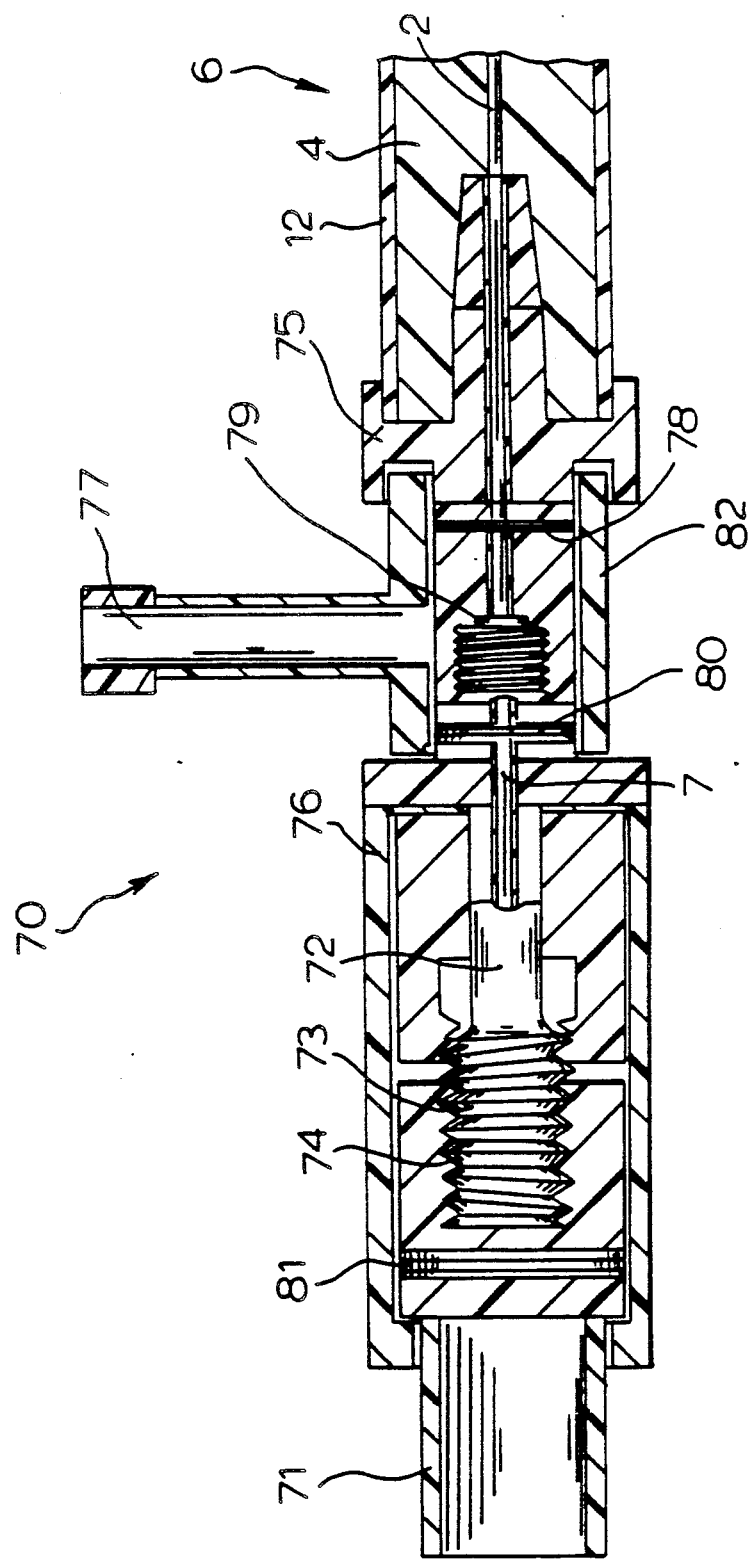
Figure 14:
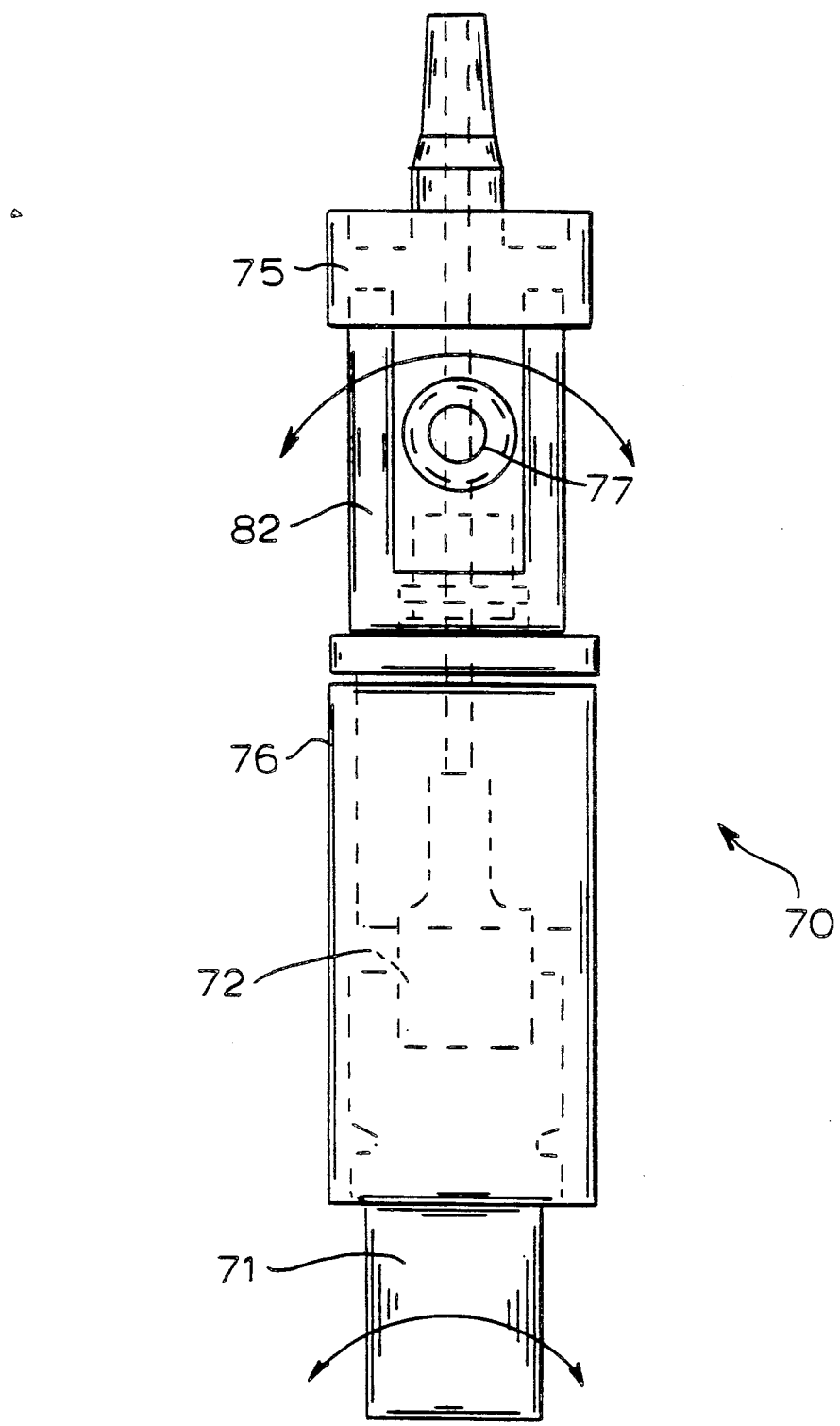

Alternate control means, generally designated as 50 and 70, are shown in FIGS. 12 to 14. Control means 50 employs a threaded or deflection knob 51 for precise tip deflection. Clockwise rotation of the deflection knob 51 causes pressure to be exerted on deflection wire termination block 52, which in turn causes pressure to be exerted distally along the longitudinal axis of deflection wire 2, which in turn causes the distal end of the catheter to deflect. When deflection knob 51 is backed out, i.e., rotated in counterclockwise fashion, a return spring 53 pushes the deflection wire termination block 52 back to its original position and thus allows the catheter tip to straighten. To rotate the catheter, rotation control knob 54 is rotated. This rotates the entire catheter body, i.e., body skin 12 and spring coil body 4, and the steering wire 2 simultaneously.

The termination block 52 has a non-circular, e.g., rectangular or square, cross-section, and any rotational movement of the termination block is limited or prevented by substantially annular sealing/guide means 57. Preferably the only movement by the termination block 52 is in the longitudinal direction, i.e., proximally or distally.

Control means 50 also has ports 55 and 56 that are in fluid communication with a through-lumen 60, which is in turn in fluid communication with the lumen 14, for passage of liquids or other devices, e.g., other catheters, guidewires, pressure monitoring means, optical fibers, and the like, through the lumen 14. Annular seals 61, preferably made of suitable polymeric material such as TEFLON, allow the port section 62 to remain stationary while the rotation control knob 54 is manipulated.

As shown in FIGS. 13 and 14, control means 70 employs a threaded control or deflection knob 71 for precise tip deflection. The proximal end 7 of the deflection wire 2 is fixedly engaged at engaging member 72, the outer surface of which has threading 73 which engages cooperating threading 74 on the inner surface of the distal portion of deflection knob 71. Rotation of deflection knob 71 causes movement of engaging member 72, which in turn causes movement of the deflection wire 2 along its longitudinal axis, which in turn causes the distal end of the catheter to deflect. The proximal end of catheter 6 is engagingly attached to attachment member 75, which is in turn connected to rotation control member 76. When rotation control member 76 is rotated, the catheter 6 is rotated, which in turn results in rotation of the distal end 10 of the catheter 6.

Port 77 is in fluid communication with lumen 14 for inflation of the dilatation balloon (not shown). Annular seals 78, 79, 80, and 81 permit the port section 82 to remain stationery while the deflection knob 72 and/or the rotation control member 76 is manipulated.

In a variation of the control means shown in FIGS. 13 and 14, not shown, a control means comprises a deflection knob having an inflation port in fluid communication with lumen 14. This arrangement is advantageous in that fewer seals are required and the external source connecting to the inflation port is less in the way.

Spring coil body 4 may be comprised of flat or round metal wire or plastic coil and may comprise one continuous coil or two or more, preferably 2 or 3, coil sections that are joined together. For example, a reduced tension section 3 could comprise a radiopaque material. Preferably spring coil body 4 is comprised of stainless steel flat wire having a cross-sectional width of from about 0.001 to 0.005 in., more preferably from about 0.002 to 0.004 in., and a cross-sectional length of from about 0.007 to 0.013 in., more preferably from about 0.008 to 0.012 in.

A spring coil 4 made from a flat, i.e., rectangular, stainless steel wire is preferred, typical dimensions of the coil being from about 0.002 to 0.500 in. i.d., from about 0.004 to 0.750 in. o.d., and from about 12 to 72 in. in length. The metal deflection wire 2 is preferably made from stainless steel. Typically the diameter of the deflection wire 2 is from about 0.003 to 0.150 in. with a tapered section (for preferential bending) having a diameter of from about 0.0005 to 0.075 in. The total steering wire length may be from about 12 to 72 in., and the length of the tapered section may range from about 0.25 to 10.0 in.

In another embodiment of the invention, not shown, the distal portion of a primary coil of spring coil body 4 extending distally from a control means may terminate at a point substantially immediately proximal to the proximal portion of balloon 5, and then a second, smaller coil would extend from the distal end of the primary coil to distal end 15a of spring coil body 4. The proximal of the second, smaller coil would be bonded by suitable means to the interior of the distal portion of the primary coil. The second coil, which may be comprised of flat or round wire, is preferably comprised of round wire having a diameter of from about 0.001 to 0.020 in. The second coil may be uniformly wound, the distal portion thereof may be more loosely wound, or the proximal portion thereof under the balloon may be more loosely wound.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A steerable dilatation catheter means comprising:
   a. a flexible catheter comprising a spring coil body defining a lumen, said spring coil body having proximal and distal ends, the distal end of said spring coil body being closed, and said spring coil body having a flexible body skin thereon;
   b. dilatation balloon means positioned adjacent to the distal end of said spring coil body, said spring coil being less tightly wound for a predetermined length at a point substantially adjacent to the distal end of said spring coil body and within the dilatation balloon means, the flexible body skin proximal to the dilatation balloon means being tight against said spring coil body, and the dilatation balloon means being inflated by fluid entering through the less tightly wound coils in said predetermined length;
   c. a deflection wire within the lumen having proximal and distal ends and being substantially co-extensive with said spring coil body, the distal end of said deflection wire being attached to the distal end of said spring coil body; and,
   d. control means attached to the proximal end of said catheter, the proximal end of said deflection wire extending to the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means having rotation means to cause said deflection wire and said catheter to rotate together to cause the distal end of said catheter to rotate about its longitudinal axis.

2. The catheter means of claim 1 which comprises an anchor wire within the lumen having proximal and distal ends, the proximal and distal ends of the anchor wire being affixed to the proximal and distal ends, respectively, of the spring coil body.

3. The catheter means of claim 1 which comprises an optical fiber within the lumen having proximal and distal ends, the distal end of the optical fiber being attached to the distal end of the catheter and the proximal end of the optical fiber extending through the control means.

4. The catheter means of claim 3, wherein the optical fiber has a pressure sensing membrane at its distal end and means at its proximal end to convert a signal from the pressure sensing membrane into an electrical signal or pulse.

5. The catheter means of claim 1 which comprises a flexible tip having proximal and distal ends, the proximal end of the flexible tip being attached to the distal end of the spring coil body.

6. The catheter means of claim 5, wherein the flexible tip is a floppy wire comprised of spring wire.

7. The catheter means of claim 6, wherein the wire comprises radiopaque material selected from the group consisting of platinum, gold, tungsten, and tantalum.

8. The catheter means of claim 1, wherein the flexible body skin comprises a flexible polymeric material selected from the group consisting of polytetrafluoroethylene, polyethylene, and polyvinyl chloride.

9. The catheter means of claim 1, wherein the spring coil body comprises two or more spring coils.

10. The catheter means of claim 9, wherein the spring coil body comprises two spring coils having respective smaller and larger diameters, the proximal end of the spring coil with the smaller diameter being bonded to the inside of the distal end of the spring coil with the larger diameter.

11. A steerable dilatation catheter means comprising:
    a. a flexible catheter comprising a spring coil body defining a lumen, said spring coil body having proximal and distal ends, the distal end of said spring coil body being closed, and said spring coil body having a flexible body skin tightly fitting thereon;
    b. dilatation balloon means positioned adjacent to the distal end of said spring coil body, said spring coil being less tightly wound for a predetermined length at a point substantially adjacent to the distal end of said spring coil body and within the dilatation balloon means, the flexible body skin proximal to the dilatation balloon means being tight against said spring coil body, and the dilatation balloon means being inflated by fluid entering through the less tightly wound coils in said predetermined length;
    c. an anchor wire within the lumen having proximal and distal ends, the proximal and distal ends of the anchor wire being affixed to the proximal and distal ends, respectively, of the spring coil body; and,
    d. control means attached to the proximal end of said catheter, said control means having rotation means to cause said catheter and anchor wire to rotate together to cause the distal end of said catheter to rotate about its longitudinal axis.

12. The catheter means of claim 11 which comprises an optical fiber within the lumen having proximal and distal ends, the distal end of the optical fiber being attached to the distal end of the catheter and the proximal end of the optical fiber extending through the control means.

13. The catheter means of claim 12, wherein the optical fiber has a pressure sensing membrane at its distal end and means at its proximal end to convert a signal from the pressure sensing membrane into an electrical signal or pulse.

14. The catheter means of claim 11 which comprises a flexible tip having proximal and distal ends, the proximal end of the flexible tip being attached to the distal end of the spring coil body.

15. The catheter means of claim 14, wherein the flexible tip is a floppy wire comprised of spring wire.

16. The catheter means of claim 15, wherein the wire comprises radiopaque material selected from the group consisting of platinum, gold, tungsten, and tantalum.

17. The catheter means of claim 11, wherein the spring coil body comprises two or more spring coils.

18. The catheter means of claim 17, wherein the spring coil body comprises two spring coils having respective smaller and larger diameters, the proximal end of the spring coil with the smaller diameter being bonded to the inside of the distal end of the spring coil with the larger diameter.

19. A steerable dilatation catheter means comprising:
  a. a flexible catheter comprising a spring coil body defining a lumen, said spring coil body having proximal and distal ends, the distal end of said spring coil body being closed, and said spring coil body having a flexible body skin tightly fitting thereon and extending from said proximal end to said distal end;
  b. dilatation balloon means positioned adjacent to said distal end of said spring coil body and concentrically around said spring coil body, said dilatation balloon means having proximal and distal portions sealingly attached to said flexible coating, and said flexible coating having an opening within said dilatation balloon means to permit inflation thereof;
  c. a deflection wire within the lumen having proximal and distal ends and being substantially co-extensive with said spring coil body, the distal end of said deflection wire being attached to the distal end of said spring coil body; and,
  d. control means attached to the proximal end of said catheter, the proximal end of said deflection wire extending to the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means having rotation means to cause said deflection wire and said catheter to rotate together to cause the distal end of said catheter to rotate about its longitudinal axis.

20. The catheter means of claim 19 which comprises an anchor wire within the lumen having proximal and distal ends, the proximal and distal ends of the anchor wire being affixed to the proximal and distal ends, respectively, of the spring coil body.

21. The catheter means of claim 19 which comprises an optical fiber within the lumen having proximal and distal ends, the distal end of the optical fiber being attached to the distal end of the catheter and the proximal end of the optical fiber extending through the control means.

22. The catheter means of claim 21, wherein the optical fiber has a pressure sensing membrane at its distal end and means at its proximal end to convert a signal from the pressure sensing membrane into an electrical signal or pulse.

23. The catheter means of claim 21, wherein the spring coil body comprises two or more spring coils.

24. The catheter means of claim 23, wherein the spring coil body comprises two spring coils having respective smaller and larger diameters, the proximal end of the spring coil with the smaller diameter being bonded to the inside of the distal end of the spring coil with the larger diameter.

25. The catheter means of claim 19 which comprises a flexible tip having proximal and distal ends, the proximal end of the flexible tip being attached to the distal end of the spring coil body.

26. The catheter means of claim 25, wherein the flexible tip is a floppy wire comprised of spring wire.

27. The catheter means of claim 26, wherein the wire comprises radiopaque material selected from the group consisting of platinum, gold, tungsten, and tantalum.

28. A steerable dilatation catheter means comprising:
  a flexible catheter comprising a spring coil body defining a lumen, said spring coil body having proximal and distal ends, a flexible tip having proximal and distal ends, the proximal end of said flexible tip being positioned a short distance distally from the distal end of said spring coil body to form a discontinuity, and a flexible covering, said flexible covering extending from the proximal end of said spring coil body along the length of said spring coil body across said discontinuity to the proximal end of said flexible tip,
  dilatation balloon means positioned concentrically around said discontinuity,
  a deflection wire having proximal and distal ends, said deflection wire extending substantially co-extensively with said spring coil body, the distal end of said deflection wire being attached to the proximal end of said flexible tip,
  an anchor wire having proximal and distal ends, the proximal end of the anchor wire being affixed to the proximal end of the spring coil body and the distal end of the anchor wire being attached to said flexible tip; and
  control means attached to the proximal end of said spring coil body and having engaging means which fixedly engages the proximal end of said deflection wire to cause said deflection wire to be displaced distally or proximally, said displacement causing the distal end of said catheter to bend out of or toward the line of its longitudinal axis, and the control means having rotation means to cause said deflection wire and said catheter to rotate together to cause the distal end of said catheter to rotate about its longitudinal axis.

29. The catheter means of claim 28, wherein the flexible tip is a floppy wire comprised of spring wire.

30. The catheter means of claim 29, wherein the wire comprises radiopaque material selected from the group consisting of platinum, gold, tungsten, and tantalum.

31. A steerable catheter set comprising:
  a. steerable catheter means comprising a spring coil body defining a lumen, said spring coil body having proximal and distal ends, the distal end of said spring coil body being open, a deflection wire having proximal and distal ends and being substantially co-extensive with said spring coil body, the distal end of said deflection wire being attached to the distal end of said spring coil body, and control means attached to the proximal end of said catheter, the proximal end of said deflection wire extending to the control means, the control means having engaging means which fixedly engages the proximal end of said deflection wire to cause said deflection wire to be displaced distally or proximally, said displacement causing the distal end of said catheter to bend out of or toward the line of its longitudinal axis, and the control means having rotation means to cause said deflection wire and said catheter to rotate together to cause the distal end of said catheter to rotate about its longitudinal axis; and,
  b. fiber optic means extending with the lumen of said steerable catheter and being passable therein.

32. The catheter means of claim 31 which comprises an anchor wire having proximal and distal ends, the proximal and distal ends of the anchor wire being affixed to the proximal and distal ends, respectively, of the spring coil body.

33. The catheter means of claim 31, wherein said spring coil body has a flexible covering comprising a flexible polymeric material.

34. The catheter means of claim 33, wherein the deflection wire is between said spring coil body and said flexible covering.

35. The catheter means of claim 33, wherein the flexible covering forms an atraumatic, annular tip at the distal end of the spring coil body.

36. The catheter means of claim 33, wherein the flexible polymeric material is polytetrafluoroethylene, polyethylene, or polyvinyl chloride.

37. The catheter means of claim 31, wherein the deflection wire is within the lumen defined by said spring coil body.

38. The catheter means of claim 31, wherein the spring coil body comprises two or more spring coils.

39. The catheter means of claim 38, wherein the spring coil body comprises two spring coils having respective smaller and larger diameters, the proximal end of the spring coil with the smaller diameter being bonded to the inside of the distal end of the spring coil with the larger diameter.

40. The catheter means of claim 31, wherein said spring coil body is less tightly wound for a predetermined length at a point substantially adjacent to the distal end of said spring coil body.

* * * * *